United States Patent [19]

Ekwall

[11] Patent Number: 5,413,109
[45] Date of Patent: May 9, 1995

[54] ELECTROCARDIOGRAPHIC APPARATUS FOR ANALYZING THE FUNCTION OF A HEART AND FOR PACING THE HEART DEPENDENT ON THE ANALYSIS

[75] Inventor: Christer Ekwall, Spanga, Sweden

[73] Assignee: Siemens Elema AB, Solna, Sweden

[21] Appl. No.: 51,249

[22] Filed: Apr. 23, 1993

[30] Foreign Application Priority Data

Dec. 18, 1992 [SE] Sweden .................................. 9203821

[51] Int. Cl.$^6$ .............................................. A61B 5/04
[52] U.S. Cl. .................................................. 128/696
[58] Field of Search ........................ 128/696, 702, 705

[56] References Cited

U.S. PATENT DOCUMENTS 4,417,306 11/1983 Citron et al. .
4,453,551 6/1984 Anderson et al. .
4,812,976 3/1989 Lundy .
4,870,578 9/1989 Vysin et al. .
4,905,708 3/1990 Davies .
5,042,497 8/1991 Shapland .

FOREIGN PATENT DOCUMENTS 0220916 5/1987 European Pat. Off. .

Primary Examiner—William E. Kamm
Assistant Examiner—Scott M. Getzow
Attorney, Agent, or Firm—Hill, Steadman & Simpson

[57] ABSTRACT

A device for analyzing the function of a heart has an electrical measurement unit for generating a measurement signal related to an electrical or mechanical heart variable, and an evaluation unit for evaluating the measurement signal. The device further includes circuitry for generating at least one parameter signal from the measurement signal. The evaluation unit analyzes related values in the measurement signal and the parameter signal, these related values corresponding to coordinates which form a curve in a coordinate system, the measurement signal and the parameter signal serving as coordinate axes, by sensing the sequence in which the curve passes a predesignated number of areas in the coordinate system. The device is capable of detecting spontaneous and stimulated heartbeats, tachyarrhythmias, retrograde conduction, ectopic beats, etc.

12 Claims, 4 Drawing Sheets

ELECTROCARDIOGRAPHIC APPARATUS FOR ANALYZING THE FUNCTION OF A HEART AND FOR PACING THE HEART DEPENDENT ON THE ANALYSIS

BACKGROUND OF THE INVENTION

1. Field of the Invention

The present invention relates to a device for analyzing the function of a heart, having a measurement unit for generating a measurement signal related to an electrical or mechanical heart variable, and an evaluation unit for evaluating the measurement signal.

2. Description Of the Prior Art

In the monitoring, diagnosis and treatment of a heart's function, accurate determination of the heart's current condition, with minimal risk of erroneous interpretations, is important. Automatic monitoring of the heart is a valuable asset in the treatment of heart disease so that a therapeutic measure can be instituted without delay when necessary.

The electrocardiogram (ECG) is one heart variable which is an indicator of a heart's function. Sensing the ECG in order to obtain a measurement signal which can be evaluated in establishing the condition of the heart is known in the art.

One way to graphically elucidate the electrocardiogram by plotting the voltage in a recorded electrocardiogram against the time derivative of the voltage is described in an article entitled "Phase Plane Plot of Electrograms as a Marker of Ventricular Electrical Instability During Acute Ischemia: Initial Experimental Results and Potential Clinical Applications", published in the journal PACE, Vol. 15, part II, November 1992, pp. 2188–2193. This procedure produces a curve corresponding to the ECG signal. The article shows that there is a relationship between changes in parts of the curve during acute ischemia and the development of ventricular fibrillation. The authors of the article state that a presentation of an electrocardiogram in graphical form can be an excellent complement to traditional, real-time presentation.

U.S. Pat. No. 4,417,306 describes an apparatus which monitors and stores heart signals. The apparatus senses the ECG, and the ECG signal must have a predesignated slope, amplitude, duration and course to be accepted as a heart beat. The QRS complex is the main segment sensed, i.e., the electrical signals which occur in the heart when there is a ventricular beat (ventricular systole).

U.S. Pat. No. 4,453,551 describes an apparatus designed to detect ventricular fibrillation (VF). The apparatus senses the ECG signal from the heart, digitizes it and amplifies it to a predetermined amplitude. The amplified signal can then be analyzed in different ways to ascertain whether or not VF is present. For example, the statistical distribution of gradients or the frequency of the maximum negative gradient can be analyzed.

European Application 0 220 916 describes an apparatus designed to detect the presence of ventricular tachycardia (VT) and VF and to supply treatment to terminate these conditions. The apparatus senses the heart's ECG at a plurality of points on the heart and determines the sequence in which the signals are detected at the different measurement points. In VT and VF, the sequence deviates from the normal pattern in different ways.

SUMMARY OF THE INVENTION

It is an object of the present invention to provide a device which analyzes the function of the heart in a reliable, efficient but still simple manner.

Another object is to provide a device which can be used for diagnosing heart defects, monitoring heart functions and adapting therapy to make treatment as safe and effective as possible.

The above objects are achieved in accordance with the principles of the present invention a device having a measurement and evaluation unit wherein the evaluation unit includes means for generating at least one parameter signal on the basis of the measurement signal, and the evaluation unit analyzes related values for the measurement signal and the parameter signal by determining whether they satisfy a predesignated number of conditions.

Instead of analyzing only one measurement signal, the device first generates a parameter signal from the measurement signal, and related signal values of the measurement signal and parameter signal are analyzed. A normally working heart (as in a healthy heart) is hemodynamically stable, and a virtually identical sequence of related values is generated from one heart cycle to another, so different conditions are satisfied in the same sequence cycle after cycle. Pathological changes and other abnormal conditions in a heart affect the satisfying of different conditions in a distinct way and can therefore be easily identified. The conditions can consist of any kind of mathematical relationship. Certain relationships for different, known changes in a specific individual can also be used.

Preferably, the related variables correspond to coordinates forming a curve in a coordinate system, with the measurement signal and parameter signal as coordinate axes, and preferably the predetermined number of conditions corresponds to a predetermined number of areas in the coordinate system, whereby the evaluation unit determines the sequence in which the curve traverses the predetermined number of areas.

Having the related values correspond to coordinates in a coordinate system results in a clarified analysis. The generated curve becomes virtually identical, from one heart cycle to another, as long as the heart functions in a constant manner.

An application filed simultaneously herewith having U.S. Ser. No. 08/051,250 entitled "Device for Analyzing the Functioning of a Heart" (Noren et al.,), filed Apr. 23, 1993 describes a device which analyzes heart-related signals by utilizing a two- or multidimensional representation of the signals.

In another embodiment of the device in accordance with the invention the means for generating at least one parameter signal from the measurement signal is a differentiator which obtains the first derivative of the measurement signal.

With the derivative of the measurement signal as a parameter, related values are obtained which, for a normal heart, form a substantially closed curve with a small loop inside a larger loop in the coordinate system. This curve changes when e.g. a VT or a VF is present. Definition of different areas the curve can pass in various heart conditions and the determining of the areas the curve passes and in which sequence the areas are passed make it possible to identify different arrhythmias and anomalies. The curve changes even when certain other specific cardiac events occur, such as retrograde conduction and extrasystoles. Spontaneous and stimulated heart beats give rise to different curves, and the device can be used for detecting both spontaneous heart beats and stimulated heart beats.

As an alternative or a complement to differentiation, the means for generating a parameter signal from the measurement signal may be or include an integrator which integrates the measurement signal.

By the use of an integrated signal, with integration occurring over a plurality of heart cycles, the system is more stable, and the curve does not wander outside the predetermined decision areas. If the integration interval is shorter than a heart cycle, a parameter signal is produced which with the measurement signal, forms a curve in the same way as the measurement signal and the measurement signal's derivative. Integration produces simultaneous filtration of noise.

An enhancement of the device is achieved in an embodiment of the invention wherein the evaluation unit has a plurality of comparators, each of which is supplied with at least one of the measurement signal or the parameter signal and an input signal. Each comparator represents a line in the coordinate system, which lines delineate the predetermined number of areas. Each corresponding comparator generates an output signal when the curve being analyzed is on one side of a specific line, associated with that comparator. The evaluation unit in this embodiment also includes a sequence analyzer for determining the sequence in which the comparators generate output signals.

Each comparator thus represents a line in the coordinate system, and the comparator's output signal is zero or one ("low" or "high"), depending on which side of the line the curve is located. With a plurality of lines, the coordinate system is subdivided into a plurality of areas which can be made larger or smaller. On the basis of the comparators' output signals, the course of the curve can be followed throughout each heart cycle and compared with various predetermined courses in order to determine the condition of the heart. The lines can be parallel to one another, perpendicular to one another, arise from a common point, arise from a plurality of points, etc.

In order to be able to shift the curve in relation to the coordinate system and additionally to form a plurality of different lines, preferably the evaluation unit further includes a reference signal generator which generates a reference signal serving as the input signal for at least one comparator.

An additional enhancement is obtained in a further embodiment of the invention including a first timer for measuring the time in which the related values satisfy at least one specific condition.

In this embodiment, therefore, information is obtained in addition to that provided by condition satisfaction itself or, when a curve is described, the course of the curve in relation to the measurement signal parameter signal (MS-PS) diagram, thereby increasing the possibility of attaining reliable identification of various conditions in the heart.

Alternately, or as an additional complementary feature, the device may include a second timer to measure the time elapsing from a time at which the relevant values satisfy a first specific condition until they satisfy a second specific condition.

In a further embodiment, the device includes a pulse generator for generating and emitting stimulation pulses to the heart according to the state of the heart as analyzed by the device.

The device can thereby supply a therapeutic measure when necessary, such as a specified pacing, antitachycardia or defibrillation sequence.

DESCRIPTION OF THE PREFERRED EMBODIMENTS

Figure 1:
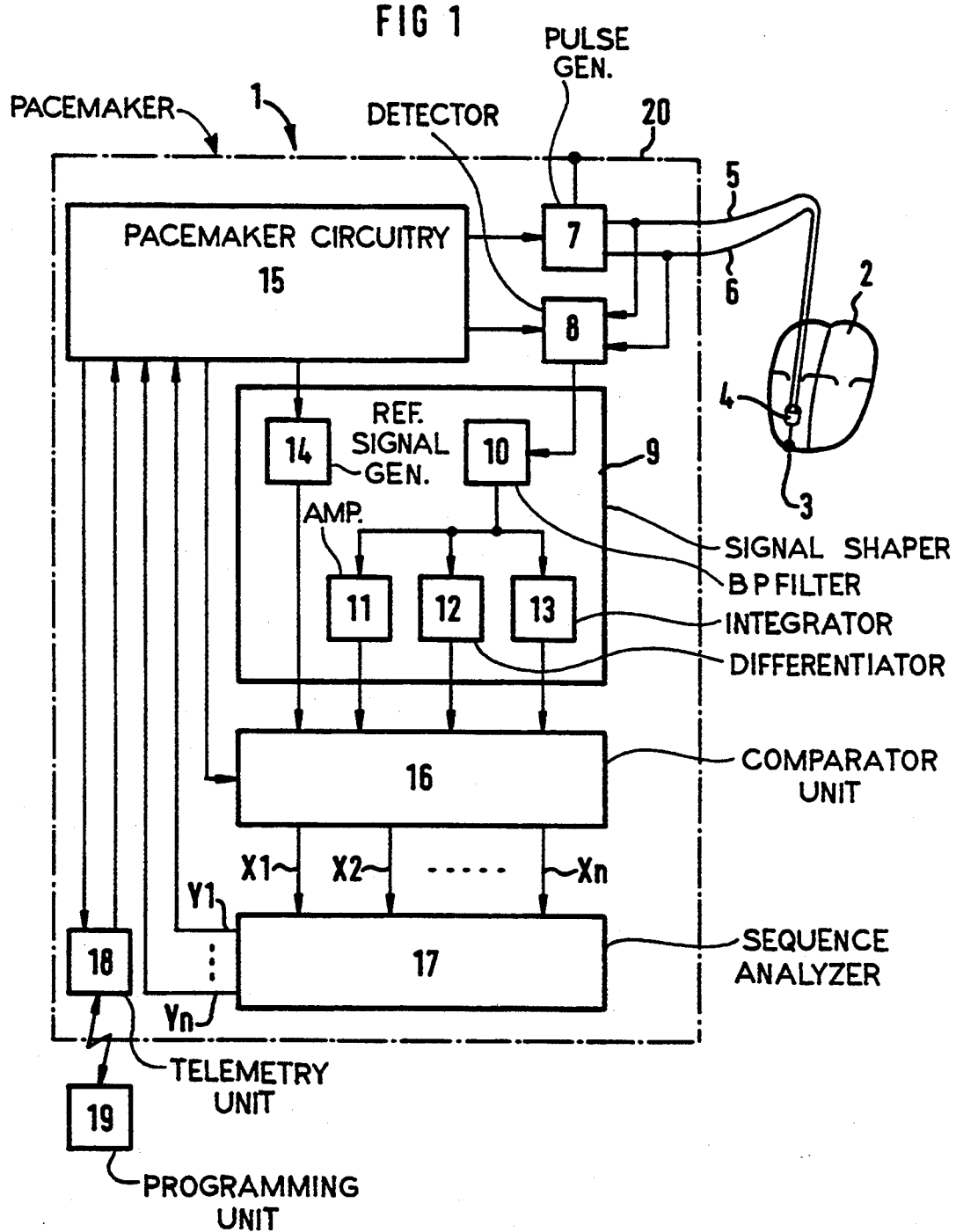
FIG. 1 shows, in block diagram form, an embodiment of the device according to the invention.

An embodiment of the invention in the form of a pacemaker 1 is shown in FIG. 1 is connected to a heart 7. A tip electrode 3 and a ring electrode 4 are placed in the right ventricle of the heart 2 and are connected, via a first electrode conductor 5 and a second electrode conductor 6 to a pulse generator 7 in the pacemaker 1. The pulse generator is also connected to pacemaker can 20 which functions as an indifferent electrode, i.e., the pulse generator 7 can either emit stimulation pulses between the tip electrode 3 and the ring electrode 4 or between the tip electrode 3 and the pacemaker can 20. A detector 8 is connected in parallel with the first electrode conductor 5 and the second electrode conductor 6. The detector 8 senses the heart's electrical activity, i.e., the ECG, and sends a measurement signal to a signal shaper 9. The signal shaper 9 first filters the signal in a bandpass filter 10. The bandpass filter 10 primarily eliminates high frequency noise which could otherwise overwhelm subsequent signal components. After filtration, the filtered signal is sent to each of an amplifier 11, a differentiator 12 and an integrator 13 which integrates the signal for a plurality of heart cycles. In this manner, three parameter signals are formed from the single measurement signal. The signal shaper 9 contains a reference generator 14 which generates a reference signal. The reference generator 14 is connected to pacemaker electronic circuitry 15 which includes e.g., a battery and microprocessor for controlling the pacemaker.

The four signals, at least two of which constitute coordinates forming a curve in a coordinate system, are sent to a comparator unit 16. The comparator unit 16 comprises a plurality of comparators representing different lines in the coordinate system. Each comparator generates an output signal when the curve is on a specific side of the line the comparator represents. So a plurality of output lines X1, X2, ..., Xn runs from the comparator unit 16 to a sequence analyzer 17 which identifies those comparators which emitted an output signal and the sequence in which this occurs. A plurality of sequence signal lines Y1, ..., Ym runs from the sequence analyzer 17 to pacemaker electronic circuitry 15, in which the microprocessor decides whether any action should be taken on the basis of the signal from the sequence analyzer 17.

A physician can, with the aid of a programming unit 19 communicate with pacemaker electronic circuitry 15 via a telemetry unit 18, in order e.g., to change the lines the comparators in the comparator unit 16 represent or in order to retrieve stored information on detected sequences and the treatment given.

Figure 2:
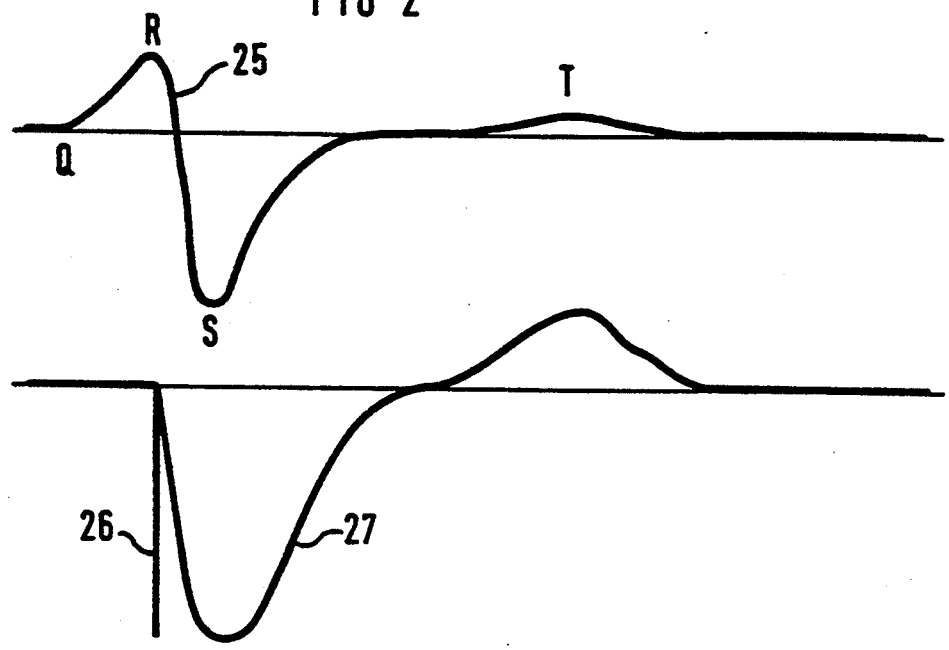
FIG. 2 shows a spontaneous heart signal and a stimulated heart signal.

FIG. 2 shows an example of two different signals which can be detected in the pacemaker 1. A spontaneous heart signal 25 is shown at the top. Here, the spontaneous heart signal 25 only shows the QRST complex in the heart signal 25, i.e., the signals generated by ventricular depolarization in systole and repolarization in diastole.

A stimulation pulse 26, resulting in a stimulated heart signal 27, is shown at the bottom. Again, only the ventricular signal is shown. As a direct comparison shows, the stimulated heart signal 27 lacks the positive R wave found in the spontaneous heart signal 25, while the negative part of the stimulated heart signal 27 is simultaneously more pronounced than the S wave in the spontaneous heart signal 25. The repolarization wave in the stimulated heart signal 27 is larger than the T wave in the spontaneous heart signal 25.

Figure 3:
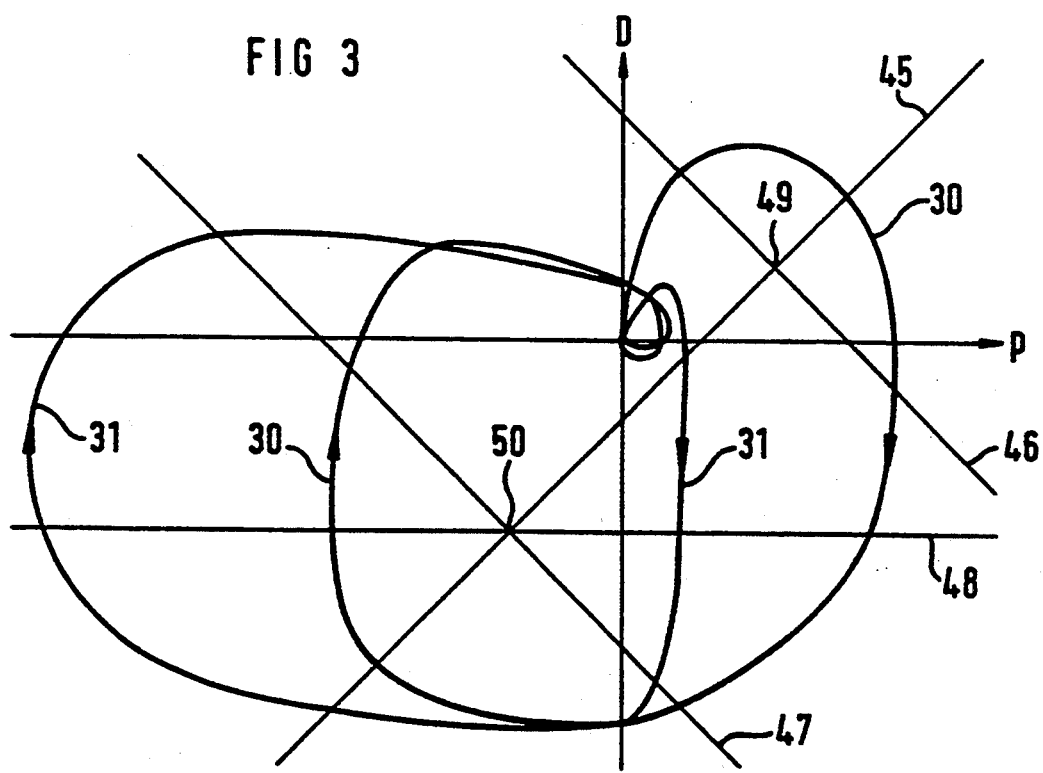
FIG. 3 is a schematic illustration, for explaining the operation of the invention.

In FIG. 3, the proportional value is plotted against the derivative for each point in time. The spontaneous heart signal 25 then generates the curve 30 and the stimulated heart signal 27 generates the curve 31.

The signal lines represented by the comparators have also been entered into the coordinate system. The comparators will be described in greater detail in conjunction with FIG. 4. As can be seen, the morphological difference between the spontaneous heart signal 25 and the stimulated heart signal 27 is depicted with greater clarity in the PD-coordinate system than in the real time diagrams in FIG. 2.

Figure 4:
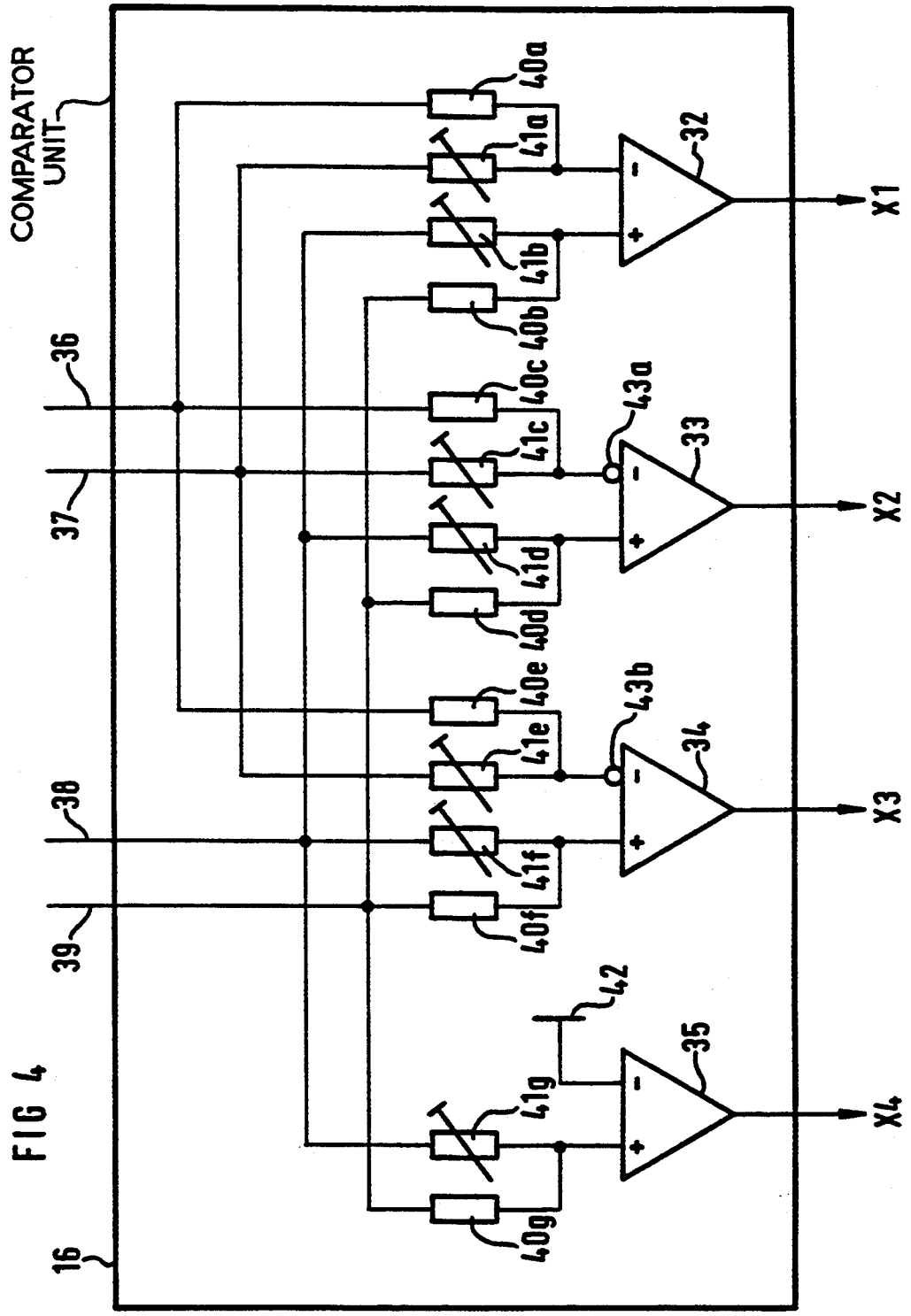
FIG. 4 shows a block diagram of a comparator unit in the device.

As noted above, the comparator unit 16 contains a plurality of comparators. FIG. 4 shows one way of constructing the comparator unit 16 With four comparators 32, 33, 34, and 35, four different limit conditions are created which respectively correspond to lines 45, 46, 47, and 48 in the PD diagram in FIG. 3. Input signals to the comparator unit 16 consist of the proportional signal in signal line 36, the integrated signal in signal line 37, the reference signal in signal line 38 and the derivative signal in signal line 39. In the first comparator 32, the proportional signal is supplied to the negative input via a first resistor 40a. The integrated signal is also supplied via a potentiometer 41a, to the negative input. The derivative signal, via a second resistor 40b, and the reference signal, via a second potentiometer 41b are supplied to the positive input. The output signal from the first comparator 32 has been designated X1, and the following conditions must be satisfied for the first comparator 32 to emit an output signal:

$$D+(C_b \cdot V_{ref}) - P - (C_a \cdot I) > 0,$$

wherein the proportional signal is generally designated P, the derivative signal is generally designated D, the integrated signal is generally designated I, the reference signal is generally designated $V_{ref}$, the resistors 40a, 40b, etc. all have the same value set at one, and the potentiometers' value in relation to the resistors is designated $C_a$ for the first potentiometer 41a, $C_b$ for the second potentiometer 41b, etc.

Thus, the first line can be written:

$$D = P + C_a I - C_b V_{ref},$$

which produces the line 45 in the PD diagram in FIG. 3. The first comparator 32 generates an output signal when the curve 30 is above the line 45.

In the corresponding manner, the proportional signal is connected, via a resistor 40c and a first inverter 43a, to the negative input in the second comparator 33. The integrated signal is also connected, via a third potentiometer 41c and the first inverter 43a, to the negative input. The derivative signal, via a fourth resistor 40d, and the reference signal, via a fourth potentiometer 41d are supplied to the positive input. The output signal from the second comparator 33 has been designated X2, and the condition $$D + C_d V_{ref} - (-P - C_c I) > 0$$

must be satisfied for an output signal to be received from the second comparator 33, i.e., the line $D = -P - C_c I - C_d V_{ref}$. This is line 46 in the PD diagram.

For the comparator 34, the proportional signal is analogously connected to the negative input, via a fifth resistor 40e and a second inverter 43b, and the integrated signal, via a fifth potentiometer 41e and the second inverter 43b. The derivative signal via a sixth resistor 40f, and the reference signal, via a sixth potentiometer 41f are supplied to the positive input. Output X3 from the third comparator 34 produces an output signal when the curve is above line 47 in the PD diagram.

The fourth comparator 35 has its negative input connected to virtual ground 42, and to the positive input are connected the derivative signal, via a seventh resistor 40g and the reference signal, via a seventh potentiometer 41g. The output X4 produces an output signal when the curve is above line 48 in the PD diagram.

As shown by the curves in the PD diagram in FIG. 3, the spontaneous curve 30 encloses both a first point 49 at the intersection of lines 45 and 46 and a second point 50 at the intersection of lines 45, 47 and 48, whereas the stimulated signal 31 only encloses the second point 50. A determination by the sequence analyzer 17 of whether the generated curve encloses both the first point 49 and the second point 50 is sufficient to distinguish spontaneous heart signals from stimulated heart signals and to determine whether the signal is spontaneous or stimulated.

More generally, the areas formed between the lines 45, 46, 47 and 48 can be said to represent different states of the device, since the combination of output signals from the comparators 32, 33, 34 and 35 are unique to each area. If, for example, starting from the origin in the PD diagram conditions for emission of a signal by the first comparator 32, the third comparator 34 and the fourth comparator 35, respectively corresponding to lines 45, 47, and 48, are satisfied, this results in a signal state of 1011 for signal outputs X1, X2, X3, X4. If each state described by a curve is recorded, a number of different heart conditions can be identified. The function of the sequence analyzer 17 can thereby be described with state sequence graphs, as shown in FIGS. 5 and 6.

Figure 5:
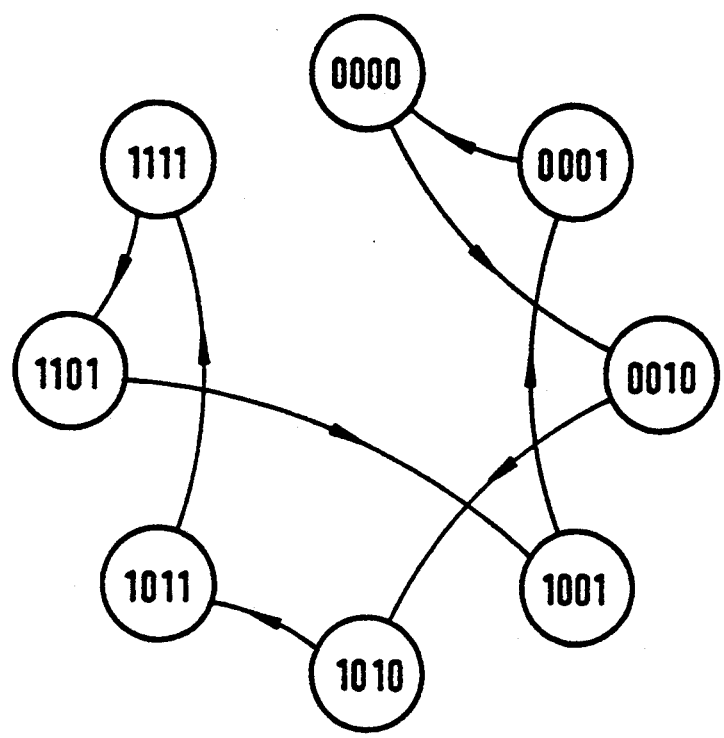
FIGS. 5 and 6 illustrates state sequences arising in the device of the invention for two different heart sequences.

FIG. 5 shows eight states, corresponding in principle to the states which can occur in the above-described embodiment. The intersection of lines 46 and 48 (not shown) results in an additional area and state which is not shown in the FIG.

The spontaneous curve shown in FIG. 3 will commence in state 1011 in the sequence graph, then cross line 46 to state 1111 and then, after crossing line 45, to state 1101, etc., traversing the entire sequence back to state 1011.

Figure 6:
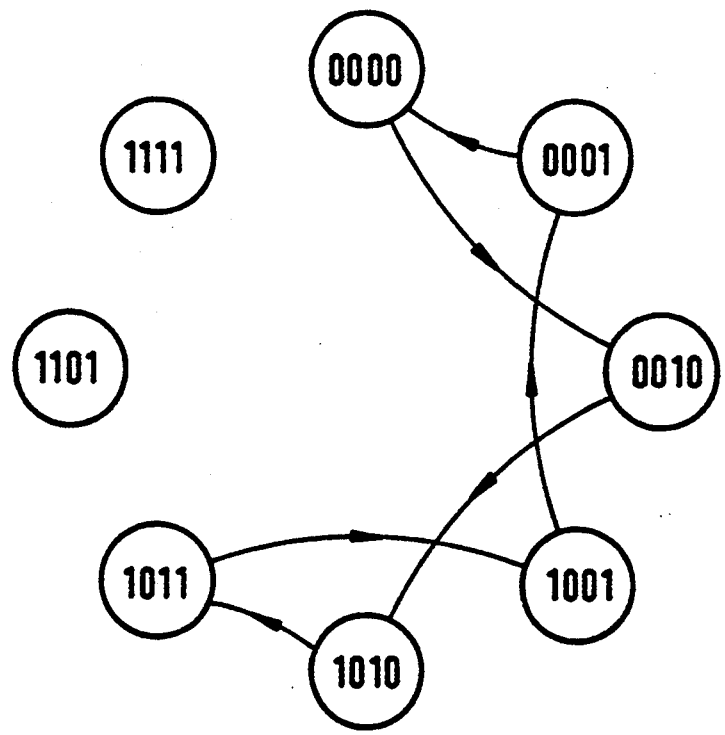

FIG. 6 shows the sequence between states covered by the stimulated signal 31. It also begins in state 1011 but subsequently crosses line 45 and goes directly to state 1011, thereafter following the same sequence as the spontaneous signal 30.

On the basis of the possible sequences a signal is able to follow, the sequence analyzer 17 can be devised to identify specific state change sequences, thereafter emitting a signal to pacemaker electronic circuitry 15 in the pacemaker 1. The lines 45 through 48 can be shifted in different ways with the potentiometers 41a through 41g so as to adapt conditions to different patients. Each sequence, or series of changes in state, corresponds to a specific morphology for the input signal, and since morphology changes in different ways in the presence of different heart conditions, such as tachyarrhythmias and extrasystoles, fast and reliable identification of the heart's current condition is achieved. If necessary, therefore, suitable therapy can be instituted immediately. Especially with patients suffering from different types of tachyarrhythmia, a pacemaker with an analyzer according to the invention can easily identify the different types and institute the therapeutic measure most appropriate to the condition in question.

To increase reliability in the identification of different heart conditions, the sequence analyzer 17 can be equipped with a timer which measures the time a generated curve is in a specific state.

Since every condition is unique, the sensing of each condition transition is not always necessary; only a few transitions need to be noted as arising in a specific way (e.g., a transition from a specific state or taking a specific amount of time to pass between two specific states), in order for a valid identification of the current heat condition to be made.

Although modifications and changes may be suggested by those skilled in the art, it is the intention of the inventors to embody within the patent warranted hereon all changes and modifications as reasonably and properly come within the scope of their contribution to the art.

We claim as our invention:

1. An electrocardiographic apparatus comprising:
   measurement means for measuring a heart variable of a heart and for generating a real-time measurement signal characterizing said heart variable;
   parameter signal generator means for generating a real-time parameter signal from said measurement signal, said measurement signal and said parameter signal having simultaneously changing values; and
   evaluation means for identifying said simultaneously changing values in real-time and for determining whether said simultaneously changing values satisfy predetermined conditions for generating an evaluation result indicative of the functioning of said heart.

2. An apparatus as claimed in claim 1, wherein said evaluation means comprises:
   means for plotting said measurement signal in real-time against said parameter signal to obtain a curve in a two-axis coordinate system and wherein said predetermined condition comprise a predetermined number of areas in said coordinate system; and
   means for identifying a sequence in which said curve traverses said predetermined number of areas, said sequence serving as said evaluation result indicative of the functioning of said heart.

3. An apparatus as claimed in claim 2 wherein said means for identifying a sequence comprises means for determining a sequence in which said curve traverses said predetermined number of areas in each heart cycle.

4. An apparatus as claimed in claim 1 wherein said parameter signal generator means comprises means for differentiating said measurement signal to obtain a differentiated signal for use as said parameter signal.

5. An apparatus as claimed in claim 1 wherein said parameter signal generator means comprises means for integrating said measurement signal to obtain an integrated signal for use as said parameter signal.

6. An apparatus as claimed in claim 1 further comprising timer means for measuring a time during which said simultaneously changing values satisfy at least one condition of said predetermined conditions, and for supplying said time to said evaluation means for use as part of said evaluation result.

7. An apparatus as claimed in claim 1 further comprising timer means for measuring a time duration from a time said simultaneously changing values satisfy a first of said predetermined conditions until said simultaneously changing values satisfy a second of said predetermined conditions, and for supplying said time duration to said evaluation means for use in generating said evaluation result.

8. An apparatus as claimed in claim 1 further comprising means, supplied with said evaluation result, for electrically stimulating said heart dependent on said evaluation result.

9. An electrocardiographic apparatus comprising:
   means for measuring a heart variable of a heart and for generating a real-time measurement signal characterizing said heart variable;
   parameter signal generator means for generating a real-time parameter signal from said measurement signal, said measurement signal and said parameter signal having simultaneously changing values;
   means for plotting a real-time curve of said simultaneously changing values in a two-axis coordinate system;
   a plurality of comparators, each comparator having at least one of said measurement signal or said parameter signal as an input signal and each comparator generating an output representing a line in said coordinate system, said lines respectively delineating a predetermined number of areas in said coordinate system, and each comparator generating an output signal when said curve is on one side of the line associated with that comparator; and
   sequence analyzer means for determining a sequence with which said comparators generate said output signals, said sequence serving as an analysis result indicative of the functioning of said heart.

10. An apparatus as claimed in claim 9 wherein said parameter signal generator means comprises means for differentiating said measurement signal to obtain a differentiated signal for use as said parameter signal.

11. An apparatus as claimed in claim 10 further comprising means for integrating said measurement signal to obtain an integrated signal, said integrated signal being supplied as an input to at least one of said comparators.

12. An apparatus as claimed in claim 11 further comprising means for generating a reference signal, said reference signal being supplied as an input signal to at least one of said comparators.

* * * * *